(12) United States Patent
Ades et al.

(10) Patent No.: US 8,962,550 B2
(45) Date of Patent: Feb. 24, 2015

(54) IDENTIFICATION OF INHIBITORS OF A BACTERIAL STRESS RESPONSE

(75) Inventors: Sarah Ellen Ades, Boalsburg, PA (US); Kenneth Charles Keiler, Boalsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 55 days.

(21) Appl. No.: 13/328,447

(22) Filed: Dec. 16, 2011

(65) Prior Publication Data

US 2012/0157375 A1    Jun. 21, 2012

Related U.S. Application Data

(60) Provisional application No. 61/424,337, filed on Dec. 17, 2010.

(51) Int. Cl.
| | | |
|---|---|---|
| *A61K 38/12* | (2006.01) | |
| *C12Q 1/18* | (2006.01) | |
| *C12Q 1/68* | (2006.01) | |
| *A61P 31/04* | (2006.01) | |

(52) U.S. Cl.
CPC . *C12Q 1/18* (2013.01); *A61K 38/12* (2013.01); *C12Q 1/6897* (2013.01); *G01N 2333/195* (2013.01)
USPC .............. 514/2.9; 435/32; 506/10; 506/18

(58) Field of Classification Search
CPC ....................................................... C12Q 1/6897
USPC ................................................. 506/1; 514/2.9
See application file for complete search history.

(56) References Cited

U.S. PATENT DOCUMENTS

| | | | |
|---|---|---|---|
| 6,994,985 B1 | 2/2006 | Werner et al. | |
| 2004/0157314 A1 | 8/2004 | Bergeron et al. | |
| 2006/0078875 A1* | 4/2006 | Benkovic et al. | ........... 435/4 |
| 2009/0143241 A1* | 6/2009 | Keiler et al. | ........... 506/9 |
| 2010/0129807 A1 | 5/2010 | Geyer | |

OTHER PUBLICATIONS

Button et al., "A Suppressor of Cell Death Caused by the Loss of σE Downregulates Extracytoplasmic Stress Responses and Outer Membrane Vesicle Production in *Escherichia coli*," J. Bact. 189:1523-1530 (2007).*
Hiratsu, et al. "The rpoE Gene of *Escherichia coli*, Which Encodes σE, is Essential for Bacterial Growth at High Temperature," J. Bact. 177:2918-2922 (1995).*
Thompson et al. , "σE regulates and is regulated by a small rna in *Escherichia coli*," J. Bact. 189:4243-4256 (2007)).*

(Continued)

*Primary Examiner* — Larry Riggs
*Assistant Examiner* — Karla Dines
(74) *Attorney, Agent, or Firm* — Husch Blackwell LLP

(57) ABSTRACT

A system, a composition, a method and a kit for identifying anti-bacterial agents are provided. The invention described herein is useful in identifying inhibitors of any bacterial stress response. Moreover, the invention can be applied to any sRNA and its target, any transcription factor and its target, and any transcription factor/sRNA pair (i.e., a transcription factor that regulates a sRNA). In particular, the present invention provides a system, a composition, a method and a kit for the identification of cyclic peptides that block the $\sigma^E$ pathway in *Escherichia coli*.

16 Claims, 7 Drawing Sheets

(56) References Cited

OTHER PUBLICATIONS

Urban et al., "Translational control and target recognition by *Escherichia coli* small RNAs in vivo," Nucl. Acids Res. 35:1018-1037 (2007).*

Kanehara et al., "YaeL (EcfE) activates the ζE pathway of stress response through a site-2 cleavage of anti-ζE, RseA," Genes Dev. 16:2147-2155 (2002).*

Johansen, et al., "Conserved small non-coding RNAs that belong to the σE regulon: role in down-regulation of outer membrane proteins" J. Mol. Biol. 364:1-8 (2006).*

Johansen et al., "Down-regulation of outer membrane proteins by noncoding RNAs: unraveling the cAMP-CRP- and sigmaE-dependent CyaR-ompX regulatory case," J. Mol. Biol. 383:1-9 (2008).*

Johansen, et al., "Conserved small non-coding RNAs that belong to the σE regulon: role in down-regulation of outer membrane proteins" J. Mol. Biol. 364:1-8 (2006)—mailed in OA Dec. 3, 2013.*

Urban et al., "Translational control and target recognition by *Escherichia coli* small RNAs in vivo," Nucl. Acids Res. 35:1018-1037 (2007)—mailed in OA Dec. 3, 2013.*

Button et al., "A Suppressor of Cell Death Caused by the Loss of σE Downregulates Extracytoplasmic Stress Responses and Outer Membrane Vesicle Production in *Escherichia coli*," J. Bact. 189:1523-1530 (2007)—mailed in OA Dec. 3, 2013.*

Hiratsu, et al. "The rpoE Gene of *Escherichia coli*, Which Encodes σE, is Essential for Bacterial Growth at High Temperature," J. Bact. 177:2918-2922 (1995)—mailed in OA Dec. 3, 2013.*

Thompson et al., "σE regulates and is regulated by a small rna in *Escherichia coli*," J. Bact. 189:4243-4256 (2007)—mailed in OA Dec. 3, 2013.*

Kanehara et al., "YaeL (EcfE) activates the ζE pathway of stress response through a site-2 cleavage of anti-ζE, RseA," Genes Dev. 16:2147-2155 (2002)—mailed in OA Dec. 3, 2013.*

Mutalik et al. Promoter Strength Properties of the Complete Sigma E Regulon of *Escherichia coli* and *Salmonella enterica* J. Bacterial. 2009, 191(23):7279.

Balbontin et al. Recognition of heptameric seed sequence underlies multi-target regulation by RybB small RNA in *Salmonella enterica* Molecular Microbiology (2010) 78(2), 380-394.

Papenfort et al. sigmaE-dependent small RNAs of *Salmonella* respond to membrane stress by accelerating global omp mRNA decay Molecular Microbiology (2006) 62(6), 1674-1688.

Gogol et al. Small RNAs endow a transcriptional activator with essential repressor functions for single-tier control of a global stress regulon PNAS Aug. 2, 2011 vol. 108 No. 31 12875-12880.

International Search Report regarding international companion case PCT/US2011/065601, filed Dec. 16, 2011.

Written Opinion of the International Searching Authority regarding international companion case PCT/US2011/065601, filed Dec. 16, 2011.

International Preliminary Report on Patentability regarding international companion case PCT/US2011/065601, filed Dec. 16, 2011.

* cited by examiner

IDENTIFICATION OF INHIBITORS OF A BACTERIAL STRESS RESPONSE

CROSS-REFERENCE TO RELATED APPLICATIONS

This application claims benefit to provisional U.S. Patent Application No. 61/424,337, filed Dec. 17, 2010, whose disclosure is herein incorporated by reference in its entirety.

FIELD OF THE INVENTION

The invention relates generally to the fields of microbiology, molecular biology, and medicine.

BACKGROUND

Antibiotic treatments have saved the lives of millions of people over the last 60 years, but the emergence of bacterial pathogens that are resistant to existing antibiotics poses a grave threat to human health. Gram-negative pathogens are particularly difficult to treat, because they can rapidly alter the composition of proteins in their envelope to adapt to a wide range of stresses, including challenges by the immune system and antibiotic treatment. A lack of knowledge of the molecular mechanisms by which these bacteria regulate the expression of envelope proteins limits understanding of interactions between pathogen and host, and prevents targeting crucial systems for development of new drugs.

The $\sigma^E$ cell envelope-sensing pathway is the major pathway used by Gram-negative bacteria to regulate outer membrane protein composition in response to stress. This pathway includes $\sigma^E$ (encoded by the rpoE gene), an alternative sigma factor activated by cell envelope stress, and sRNAs that act in concert with the Hfq protein to control outer membrane protein expression. The $\sigma^E$ cell envelope-sensing pathway has been shown to be critical for virulence in important pathogens including *Escherichia coli, Salmonella enterica serovar typhi, Vibrio cholerae, Burkholderia pseudomallei* and *cenocepacia*, and *Yersinia enterocolitica* (Rowley et al., *Nat. Rev. Microbiol.* vol. 4:383-394, 2006; Flannaban and Valvano, *Microbiology* vol. 154:643-653, 2008).

Studies of genetic mutations in components of this pathway has led to a basic understanding of how the pathway functions in bacterial physiology and virulence (Hayden and Ades, *PLoS ONE* vol. 3:e1573, 2008; Rowley et al., *Nat. Rev. Microbiol.* vol. 4:383-394, 2006). However, bacteria with mutations that inactivate key components of the pathway have pleiotropic defects and readily acquire suppressor mutations, making detailed physiological studies extremely difficult.

SUMMARY

A system, a composition, a method and a kit for identifying an inhibitor of a bacterial stress response are described herein. The system for identifying inhibitors of a bacterial stress response includes at least one candidate inhibitor of a bacterial stress response, a first bacterial strain, a second bacterial strain of the same species, and a culture medium that is used both for the first and second bacterial strains.

The first bacterial strain contains a nucleotide sequence having a first nucleic acid encoding $\sigma^E$, a second nucleic acid encoding RybB small RNA (sRNA), at least one transcriptional terminator sequence disposed between the first and second nucleic acids, and a nucleotide sequence comprising a third nucleic acid encoding a reporter protein. The second nucleic acid is operably linked to the first nucleic acid and the third nucleic acid is operably linked to a porin regulatory sequence. The strain also contains at least one mutation that permits growth of the bacterial strain in the absence of $\sigma^E$ activity.

The second bacterial strain of the same species as the first bacterial strain includes a nucleotide sequence comprising the third nucleic acid encoding a reporter protein and at least one mutation that permits the growth of the bacterial strain in the absence of $\sigma^E$ activity. The third nucleic acid is operably linked to the porin regulatory sequence.

A contemplated method can identify an inhibitor of a bacterial stress response. The method includes providing a first and a second bacterial strain in the same type of culture medium. The first bacterial strain contains a nucleotide sequence having a first nucleic acid encoding $\sigma^E$, a second nucleic acid encoding RybB sRNA, at least one transcriptional terminator sequence disposed between the first and second nucleic acids, and a nucleotide sequence comprising a third nucleic acid encoding a reporter protein, and at least one mutation that allows the growth of the bacterial strain in the absence of $\sigma^E$ activity. The second nucleic acid is operably linked to the first nucleic acid and the third nucleic acid is operably linked to a porin regulatory sequence.

The second bacterial strain includes a nucleotide sequence comprising the third nucleic acid encoding a reporter protein and at least one mutation that allows the growth of the bacterial strain in the absence of $\sigma^E$ activity. The third nucleic acid is operably linked to the porin regulatory sequence.

The method further includes inducing protein expression of the first bacterial strain for $\sigma^E$. Also, the method includes providing at least one candidate inhibitor of a bacterial stress response to the first and second bacterial strains.

Following the addition of the candidate inhibitor to the first and second bacterial strains, the baseline expression of the reporter protein in the first and second bacterial strains is measured.

Also included in the method is inducing protein expression of the first and second bacterial strains for the reporter protein. This inducement is followed in turn by measuring the expression of the reporter protein in the first and second bacterial strains. The expression of the first and second strains is then compared. This method further includes isolating and identifying the at least one candidate inhibitor of a bacterial stress response that does not inhibit expression of the reporter protein.

The reporter protein can be a luminescent or fluorescent protein, and the means for detecting and measuring expression of the reporter protein can include a luminometer, a fluorometer, or a fluorescence activated cell sorter. In one embodiment, the means for detecting and measuring expression of the reporter protein includes a fluorescence activated cell sorter.

In another embodiment, a composition is provided that includes a cyclic peptide inhibitor of the $\sigma^E$ pathway in an amount effective for inhibiting growth of pathogenic bacterial cells and/or blocking the ability of pathogenic bacterial cells to cause disease in a mammal, and a pharmaceutically acceptable carrier. The cyclic peptide inhibitor can be an antibiotic.

The contemplated pathogenic bacterial cells can be gram-negative bacterial cells, e.g., *Escherichia coli, Salmonella enterica serovar typhi, Vibrio cholerae, Burkholderia pseudomallei*, and *Yersinia enterocolitica*. The cyclic peptide inhibitor can modulate at least one activity such as: Hfq activity, binding of Hfq to RybB, RybB activity, ompA or ompC mRNA stability, $\sigma^E$-dependent transcription, and cellular levels of e.

Also described herein is a composition that contains a nucleotide sequence including a first nucleic acid encoding $\sigma^E$ operably linked to a second nucleic acid encoding RybB and having the at least one transcriptional terminator sequence being disposed between the first and second nucleic acids. A nucleotide sequence containing a third nucleic acid encoding a reporter protein, the third nucleic acid operably linked to a porin regulatory sequence; and at least one mutation that allows growth of the bacterial cell in the absence of $\sigma^E$ activity are also included. The contemplated bacterial cells are typically those that are used for screening the strain for identifying inhibitors of a bacterial stress response. The reporter protein can be a luminescent or fluorescent protein (e.g., YFP). The first nucleic acid can include an rpoE sequence, the second nucleic acid can include rybB sequence, and the porin regulator sequence can include ompC regulatory sequences.

In another embodiment, the method includes providing a culture of bacterial cells as described herein; introducing a library (e.g., cyclic peptide library) into the plurality of bacterial cells under conditions such that at least the third nucleic acid is transcribed. The cells are then analyzed for expression of the reporter protein. Molecules of the library that do not inhibit expression of the reporter protein are isolated and identified as candidate inhibitors of the bacterial stress response.

In the method, the reporter protein can be a fluorescent (e.g., YFP) or luminescent protein, and the step of analyzing the plurality of bacterial cells for expression of the reporter protein can include detecting fluorescence or luminescence. The bacterial stress response can include the $\sigma^E$ cell envelope-sensing pathway. The bacterial cells can be gram-negative bacterial cells, such as *Escherichia coli* cells. The first nucleic acid can include rpoE, the second nucleic acid can include rybB, and the porin regulator sequence can include ompC regulatory sequences. The method can further include the step of subjecting each candidate inhibitor to at least one secondary screen for reducing false positives and/or identifying candidate inhibitors with strong inhibitory activity, and/or the step of generating a dose-response curve for each candidate inhibitor.

In another embodiment, a method of screening for an antibiotic includes providing a cell comprising a reporter system, the reporter system including a first nucleic acid operably linked to a reporter sequence, and a second nucleic acid encoding $\sigma^E$ operably linked to a third nucleic acid encoding RybB protein; contacting the cell with a candidate antibiotic; and measuring the level of expression of the reporter sequence. In this method, an antibiotic is identified by an increase in expression compared to a control. The first nucleic acid can be an ompC gene or portion thereof, and the reporter sequence can be yfp. The cell can further include at least one mutation that allows growth of the cell in the absence of $\sigma^E$ activity. The level of expression can be measured by reporter output (e.g., fluorescence). The $\sigma^E$ can be expressed from heterologous nucleic acid, the candidate antibiotic can be from a library of compounds or from a library of peptides, and the screen can be a high-throughput screen.

In a further embodiment, a kit for screening for an antibiotic includes at least one candidate antibiotic, a first bacterial strain including a nucleotide sequence containing a first nucleic acid encoding $\sigma^E$; a second nucleic acid encoding RybB, where the second nucleic acid is operably linked to the first nucleic acid; at least one transcriptional terminator sequence disposed between the first and second nucleic acids; a nucleotide sequence containing a third nucleic acid encoding a reporter protein where the third nucleic acid is operably linked to a porin regulatory sequence; a second bacterial strain including a nucleotide sequence comprising the third nucleic acid encoding a reported protein and at least one mutation that allows the growth of the bacterial strain in the absence of $\sigma^E$ activity; a solid substrate for containing the bacterial cells; and instructions for use. The kit can further include a plurality of control bacterial cells.

Also described herein is a method of inhibiting bacterial growth on a solid surface. The method includes providing a composition including an inhibitor of a bacterial stress response identified by the composition, method and kits described herein; and coating the solid surface with the composition in an amount effective for inhibiting bacterial growth on the solid surface. The solid surface can be at least one surface of a medical device.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

The term "gene" refers to a nucleic acid molecule that codes for a particular protein, or in certain cases, a functional or structural RNA molecule.

As used herein, a "nucleic acid" or a "nucleic acid molecule" indicates a chain of two or more nucleotides such as RNA (ribonucleic acid) and DNA (deoxyribonucleic acid).

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

When referring to a nucleic acid molecule or polypeptide, the term "native" refers to a naturally-occurring (e.g., a wild type, WT) nucleic acid or polypeptide.

"Operably linked" as used herein may mean a functional linkage between two polynucleotides, for example a first polynucleotide and a second polynucleotide, wherein expression of one polynucleotide affects transcription and/or translation and/or mRNA stability of the other polynucleotide.

A "well" refers to a bounded area within a container, which may be either discrete (e.g., to provide for an isolated sample and/or a plurality of cells) or in communication with one or more other bounded areas (e.g., to provide for fluid communication between one or more samples and/or a plurality of cells in a well). For example, cells grown on a substrate are normally contained within a well that may also contain culture medium for living cells. Substrates can include any suitable material, such as plastic, glass, and the like. Plastic is conventionally used for maintenance and/or growth of cells in vitro.

A "multi-well vessel," as noted above, is an example of a substrate including more than one well in an array. Multi-well vessels useful in the method, kit and composition described herein can be of any of a variety of standard formats (e.g., plates having 2, 4, 6, 24, 96, 384, or 1536, etc., wells), but can also be in a non-standard format (e.g., plates having 3, 5, 7, etc., wells).

A "high throughput screen" or "HTS" as used herein refers to a method that provides for multiple candidate agents, samples or test compounds to be screened simultaneously. As further described below, examples of such methods may include the use of microtiter plates that are especially convenient because a large number of methods can be carried out simultaneously, using small amounts of reagents and samples. The methods are easily carried out in a multi-well format including, but not limited to 96-well and 384-well formats and can be automated.

As used herein, the term "anti-microbial agent" encompasses any molecule, chemical entity, composition, drug, therapeutic agent, or biological agent capable of preventing or reducing growth of a microbe, or capable of blocking the ability of a microbe to cause disease. An example of an anti-microbial agent is an antibiotic. This term includes small molecule compounds, antisense reagents, siRNA reagents, antibodies, enzymes, peptides organic or inorganic molecules, natural or synthetic compounds and the like.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Figure 1:
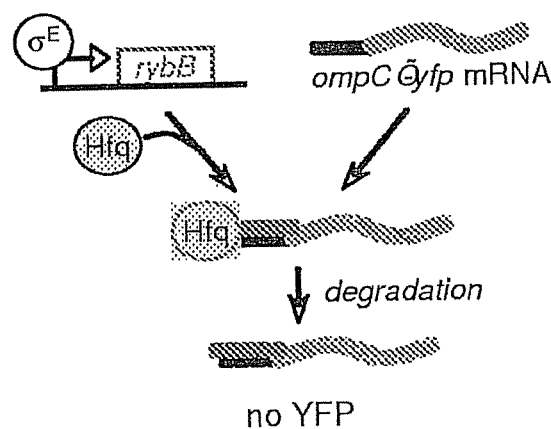
FIG. 1 is an overview of one embodiment of the composition, method and kit described herein. A yfp gene was engineered with a sequence from the ompC gene, placing it under control of the $\sigma^E$ system. When the system is functional, $\sigma^E$ directs transcription of the rybB sRNA, and the RybB-Hfq complex targets the yfp mRNA for degradation, so no YFP is made and cells will be dark. Inhibitors that block either transcription of RybB by $\sigma^E$ or RybB-Hfq activity will result in production of YFP and fluorescent cells.

In *Escherichia coli*, $\sigma^E$ is essential for the homeostasis of the cell envelope during stress and growth. Described herein is a system, a composition, a method, and a kit for identifying inhibitors of the $\sigma^E$ pathway. Such an inhibitor can render bacterial pathogens harmless. This invention contemplates $\sigma^E$ acting to promote the transcription of the rybB sRNA, which works in conjunction with the Hfq protein to degrade the ompC mRNA. The reporter system fuses ompC with the gene yfp encoding yellow fluorescent protein. According to the pathway, when $\sigma^E$ activity is high, RybB will be produced, and there will be low fluorescence. The opposite is also true; if $\sigma^E$ activity is low, ompC-yfp transcription will be undisturbed and high fluorescence will be observed.

An inventive system, composition, method and kit can be used in a high throughput screen (HTS) to identify small molecule inhibitors of the two critical steps in the $\sigma^E$ pathway: transcription by $\sigma^E$ and regulation of outer membrane porin synthesis by $\sigma^E$-dependent sRNAs. The targeted components of the pathway are widely conserved. Therefore, the inhibitors are applicable to many bacterial pathogens, even if initially isolated in *E. coli*. These inhibitors also provide essential tools to examine the $\sigma^E$ system in pathogens that are not amenable to genetic analysis. In addition to enabling critical physiological methods, the inhibitors can be used to dissect the biochemical mechanisms that underlie transcription by $\sigma^E$ and sRNA-Hfq function. Finally, these inhibitors provide lead compounds for antibiotic development targeting the $\sigma^E$ envelope-sensing pathway.

Biological and Library Methods

Methods involving conventional molecular biology techniques generally known in the art are described in detail in methodology treatises such as *Molecular Cloning: A Laboratory Manual*, 3rd ed., vol. 1-3, ed. Sambrook et al., Cold Spring Harbor Laboratory Press, Cold Spring Harbor, N.Y., 2001; and *Current Protocols in Molecular Biology*, ed. Ausubel et al., Greene Publishing and Wiley-Interscience, New York, 1992 (with periodic updates). Construction and use of a SICLOPPS (Split Intein Circular Ligation of Proteins and Peptides) library is described in Scott et al., *Proc. Natl. Acad. Sci.* vol. 96:13638-13643, 1999; Tavassoli et al., *Nature Prot.* vol. 12:1126-1133, 2007; and U.S. Pat. No. 7,354,756. Patents and technical literature provide numerous technical methodologies for the preparation of compound libraries. (See, e.g., U.S. Pat. No. 5,010,175; Furka (1991) *Int. J. Pept. Prot. Res.* 37:487-493; Houghton et al. (1991) *Nature* 354: 84-88; PCT Publication No. WO 91/19735; PCT Publication No. WO 93/20242; PCT Publication No. WO 92/00091; U.S. Pat. No. 5,288,514; Hobbs et al. (1993) *Proc. Nat. Acad. Sci. USA* 90:6909-6913; Hagihara et al. (1992) *J. Amer. Chem. Soc.* 114:6568; Hirschmann et al. (1992) *J. Amer. Chem. Soc.* 114:9217-9218; Chen et al. (1994) *J. Amer. Chem. Soc.* 116: 2661; Cho et al. (1993) *Science* 261:1303; Campbell et al. (1994) *J. Org. Chem.* 59:658; U.S. Pat. No. 5,539,083; Vaughn et al. (1996) *Nature Biotechnology* 14:309-314; PCT/US96/10287; Liang et al. (1996) *Science* 274:1520-1522 and U.S. Pat. No. 5,593,853.)

A System, a Composition, a Method and a Kit for Identifying Inhibitors of a Bacterial Stress Response The system, composition, method, and kit described herein find particular use in identifying inhibitors of any bacterial stress response. The invention described herein can be applied to any sRNA and its target, any transcription factor and its target, and any transcription factor/sRNA pair (i.e., a transcription factor that regulates a sRNA). One important bacterial stress response system is the $\sigma^E$ pathway system. A contemplated system for identifying inhibitors of a bacterial stress response includes at least one candidate inhibitor of a bacterial stress response, a first bacterial strain (also referred to herein as the "reporter strain"), a second bacterial strain of the same species as the first bacterial strain, and one culture medium that is used both for the first bacterial strain and for the second bacterial strain. The first bacterial strain is a plurality of bacterial cells that includes a nucleotide sequence that contains a first nucleic acid encoding $\sigma^E$ and a second nucleic acid encoding RybB. The second nucleic acid is operably linked to the first nucleic acid. Also, at least one transcriptional terminator sequence disposed between the first and second nucleic acids.

Furthermore, the first bacterial strain includes a nucleotide sequence comprising a third nucleic acid encoding a reporter protein. The third nucleic acid is operably linked to a porin regulatory sequence. The reporter protein is under control of the $\sigma^E$ system pathway. The first bacterial strain also contains at least one mutation that permits the growth of the bacterial strain in the absence of $\sigma^E$ activity.

A second bacterial strain of the same species as the first bacterial strain is included in the system. The second bacterial strain includes a nucleotide sequence comprising the third nucleic acid encoding a reporter protein and at least one mutation that allows the growth of the bacterial strain in the absence of $\sigma^E$ activity. The third nucleic acid is operably linked to the porin regulatory sequence. The system also includes one culture medium that is used for the first bacterial strain and the second bacterial strain.

The system can also include a means for detecting, measuring and comparing expression of the reporter protein. In addition, the system can include a means for isolating and identifying the inhibitors of the bacterial stress response.

In one embodiment, the reporter protein of the system includes a luminescent or fluorescent protein. The means for detecting and measuring expression of the reported protein can include a luminometer, a fluorometer, or fluorescence activated cell sorter (FACS).

It is contemplated that the at least one candidate inhibitor of a bacterial stress response includes a cyclic peptide or a library of cyclic peptides.

In one embodiment, the first nucleic acid includes rpoE, the second nucleic acid includes rybB, and the porin regulator sequence includes one or more ompC regulatory sequences.

A contemplated composition for identifying inhibitors of a bacterial stress response includes at least one candidate inhibitor of a bacterial stress response; a bacterial strain, and a culture medium. The bacterial strain contains a nucleotide sequence that includes a first nucleic acid encoding $\sigma^E$ and a second nucleic acid encoding RybB. The second nucleic acid is operably linked to the first nucleic acid with at least one transcriptional terminator sequence disposed between the first and second nucleic acids.

The bacterial strain includes a nucleotide sequence comprising a third nucleic acid encoding a reporter protein. The third nucleic acid is operably linked to a porin regulatory sequence.

The composition further includes a means for detecting, measuring and comparing expression of the reporter protein. The composition also includes a means for isolating and identifying the inhibitors of the bacterial stress response.

It is contemplated that the reporter protein of the composition includes a luminescent or fluorescent protein. Accordingly, the means for detecting and measuring expression of the reported protein includes a luminometer, a fluorometer or fluorescence activated cell sorter (FACS).

The at least one candidate inhibitor of a bacterial stress response includes a cyclic peptide or library of cyclic peptides.

In the composition, the first nucleic acid includes rpoE, the second nucleic acid includes rybB, and the porin regulator sequence includes one or more ompC regulatory sequences.

In addition to the system and composition, a method of identifying inhibitors of a bacterial stress response is contemplated herein. This method includes providing a culture medium containing a first bacterial strain, providing a second bacterial strain in the same type of culture medium of the first bacterial strain, inducing protein expression of the first and second bacterial strains for $\sigma^E$, providing at least one candidate inhibitor of a bacterial stress response to the first and second bacterial strains, measuring the baseline expression of the reporter protein in the first and second bacterial strains, inducing protein expression of the first and second bacterial strains for the reporter protein, measuring the expression of the reporter protein in the first and second bacterial strains, comparing the expression of the reported protein in the first and second bacterial strains, and isolating and identifying the at least one candidate inhibitor of a bacterial stress response that does not inhibit expression of the reporter protein. The first bacterial strain comprises a nucleotide sequence that includes a first nucleic acid encoding $\sigma^E$ and a second nucleic acid encoding RybB. The second nucleic acid is operably linked to the first nucleic acid. Also, at least one transcriptional terminator sequence disposed between the first and second nucleic acids.

The first bacterial strain also contains a nucleotide sequence comprising a third nucleic acid encoding a reporter protein. The third nucleic acid is operably linked to a porin regulatory sequence.

The second bacterial strain includes a nucleotide sequence that contains the third nucleic acid encoding a reporter protein and at least one mutation that allows the growth of the second bacterial strain in the absence of $\sigma^E$ activity. The third nucleic acid is operably linked to the porin regulatory sequence.

The method further can include at least one secondary screen. The at least one secondary screen includes bacterial strains constructed to distinguish between inhibitors of $\sigma^E$-dependent transcription and inhibitors RybB-Hfq activity.

It is contemplated that the at least one bacterial strain contains a reporter fusion in which a cfp gene is transcribed from a $\sigma^E$-dependent rpoHP3 promoter.

In another embodiment, the at least one bacterial strain comprises an ompC'-yfp reporter and a $\sigma^{70}$-dependent Ptrc promoter.

In still another embodiment, the first nucleic acid comprises rpoE, the second nucleic acid comprises rybB, and the porin regulator sequence comprises ompC regulatory sequences.

The reporter protein of the method is a fluorescent or luminescent protein. It is contemplated that the reporter protein is YFP.

In the method, the at least one candidate inhibitor of a bacterial stress response is a cyclic peptide or a cyclic peptide library.

A kit for screening for an antibiotic also contemplated herein. The kit includes at least one candidate antibiotic, a first bacterial strain that includes a nucleotide sequence containing a first nucleic acid encoding $\sigma^E$, a second nucleic acid encoding RybB that is operably linked to the first nucleic acid, at least one transcriptional terminator sequence disposed between the first and second nucleic acids, a nucleotide sequence comprising a third nucleic acid encoding a reporter protein that is operably linked to a porin regulatory sequence, a second bacterial strain including a nucleotide sequence containing the third nucleic acid encoding a reporter protein and at least one mutation that allows the growth of the bacterial strain in the absence of $\sigma^E$ activity, and instructions for use. It is contemplated that the third nucleic acid is operably linked to the porin regulatory sequence.

In any embodiment, the reporter protein can be any suitable reporter protein, for example, a luminescent or fluorescent protein. In the studies described herein, the reporter protein YFP was employed. Examples of additional reporter proteins that can be used include cyan fluorescent protein (CFP), green fluorescent protein (GFP), luciferase, or an enzyme with accompanying detection method such as beta-galactosidase.

In one embodiment, the first nucleic acid includes rpoE, the second nucleic acid includes rybB, and the porin regulator sequence includes one or more ompC regulatory sequences. However, other porin regulatory sequences, and $\sigma^E$-responsive sequences other than rybB can be used.

The inventions described herein can be adapted to other systems. For example, transcription factor/sRNA pairs, i.e. transcription factors that in the native context transcribe sRNA genes similar to $\sigma^E$ and rybB, can be targeted. Here, the rpoE gene is replaced by the transcription factor and the rybB gene is replaced by the sRNA (transcription termination sequences remain in between the genes). The regulatory sequence targeted by the sRNA then replaces the regulatory sequence from the ompC gene that is fused to yfp. Examples of such pairs include: $\sigma^E$ transcribes the MicA sRNA that targets sequences in the ompA gene; OmpR regulates the promoter of the MicF sRNA that targets the OmpF porin mRNA; and Fnr regulates the promoter of the FnrS sRNA that targets the SodB mRNA.

As another example, the transcriptional regulation step alone can be targeted, i.e., replace the rpoE gene with a gene encoding the transcription factor, and replace the promoter of rybB with a promoter regulated by the transcription factor of interest.

In yet another example, the sRNA step only can be targeted, i.e., replace the rybB gene with another sRNA, and replace the regulatory sequence from ompC with the sequence targeted by the sRNA.

In the case of the $\sigma^E$ pathway system, the first bacterial strain typically includes at least one mutation that allows growth of the bacterial cell in the absence of $\sigma^E$ activity because $\sigma^E$ is essential for viability. Similar suppressor mutations can be included on the chromosome if known for other transcription factors that are essential in the bacterial strain. Any of the nucleic acids present in the reporter strain can be chromosomally or heterologously expressed.

Any suitable substrate can be used. In the studies described herein, a multi-well format was used. Thus, for example, the substrate can be a 96, 384, or 1536-well format.

An example of a second bacterial (control) strain is one that includes: a nucleotide sequence including the third nucleic acid that encodes a reporter protein and that is operably linked to a porin regulatory sequence and at least one mutation that allows growth of the bacterial cell in the absence of $\sigma^E$ activity. One example of a control strain is one that contains both the third nucleic acid (encoding a reporter protein, e.g., YFP) and an empty vector lacking rpoE and rybB. In such a control strain, the third nucleic acid (e.g., ompC-yfp) is not targeted for degradation, and the reporter protein (e.g., YFP) expression is maximal. In the system, composition, method and kit described herein, dose-dependent inhibition can be measured, and inhibitors of any bacterial stress response can be identified. Inhibitors of the $\sigma^E$ cell envelope-sensing pathway can be identified. Such inhibitors can modulate one or more of the following activities: Hfq activity, binding of Hfq to RybB, RybB activity, ompA or ompC mRNA stability, $\sigma^E$-dependent transcription, degradation of targeted mRNA by RNases, and cellular levels of $\sigma^E$.

After an anti-microbial agent is identified, pharmacokinetic profiling can be pursued by the administration of an amount of the agent to an animal host (a suitable animal model). After further efficacy and safety analysis, the drug can be administered to a human patient to treat or ameliorate the symptoms of disease caused by a bacterial infection).

Antibiotic Composition and Method of Identifying Antibiotics

Described herein is a composition including an antibiotic. In one example, the antibiotic is a cyclic peptide inhibitor of the $\sigma^E$ pathway identified by the methods described herein. Such an inhibitor can reduce virulence or inhibit growth of a microbe. A typical composition includes a cyclic peptide inhibitor of the $\sigma^E$ pathway in an amount effective for blocking a RybB/Hfq-dependent step in bacterial cells present in a mammal (e.g., human), and a pharmaceutically acceptable carrier. In another example, a composition includes a cyclic peptide inhibitor of the $\sigma^E$ pathway in an amount effective for inhibiting growth of pathogenic bacterial cells in a mammal (e.g., human), and a pharmaceutically acceptable carrier. Pathogenic bacterial cells include gram-negative bacterial cells. Examples of pathogenic gram-negative bacterial cells include: *Escherichia coli, Salmonella enterica serovar typhi, Vibrio cholerae, Burkholderia pseudomallei*, and *Yersinia enterocolitica*. In a contemplated composition, the antibiotic (e.g., cyclic peptide inhibitor) modulates one or more of the following activities: Hfq activity, binding of Hfq to RybB, RybB activity, ompA or ompC mRNA stability, $\sigma^E$-dependent transcription, and cellular levels of $\sigma^E$.

A contemplated method of screening for an antibiotic includes providing a cell (e.g., a plurality of cells) that includes a reporter system. In a method of screening for antibiotics that target the $\sigma^E$ bacterial stress response, a reporter system includes: a first RybB target nucleic acid (e.g., ompC gene) operably linked to a reporter sequence (e.g., yfp), and a second nucleic acid encoding $\sigma^E$ operably linked to a third nucleic acid encoding RybB sRNA. In the method, a plurality of cells each including the reporter system are contacted with at least one candidate antibiotic (e.g., a library of small molecules), and the level of expression of the reporter sequence is measured. In this method, an antibiotic is identified by an increase in expression compared to a control, wherein the level of expression is measured by reporter output (e.g., fluorescence). Typically, the cells include at least one mutation that allows growth of the cell in the absence of $\sigma^E$ activity. The $\sigma^E$ can be expressed from a heterologous nucleic acid or chromosomally. The at least one candidate antibiotic is generally from a library of compounds. The screen can be a high-throughput screen. The plurality of cells can be any type of bacterial cell, e.g., gram-negative bacterial cells. In the experiments described herein, *Escherichia coli* cells were used to screen for candidate antibiotics.

HTS Screening for Anti-Microbial Agents

Described herein are methods for screening molecules, compounds, etc., for anti-microbial activity (e.g., antibiotics). Such methods can include, for example, small molecule screening and other compound screening. The candidate anti-microbial agents (e.g., compounds, candidate therapeutic agents, candidate agents, test compounds) can be any organic, inorganic, small molecule, protein, antibody, aptamer, nucleic acid molecule, or synthetic compound. Candidate compounds identified by methods described herein as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate or potential anti-microbial agent dc22 can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced. The candidate or potential anti-microbial agents can be obtained using any of the numerous approaches in combinatorial library methods known in the art, including: biological libraries; peptoid libraries (libraries of molecules having the functionalities of peptides, but with a novel, non-peptide backbone that are resistant to enzymatic degradation but that nevertheless remain bioactive); spatially addressable parallel solid phase or solution phase libraries; synthetic library methods requiring deconvolution; the one-bead one-compound library method; and synthetic library methods using affinity chromatography selection.

One or more methods can be used to identify a candidate anti-microbial agent (e.g., antibiotic). Manual methods, semi-automated methods, and automated methods are all possible. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BIODOT (Microdrop Model 3000).

When the method described herein is performed in a multi-well format, a suitable device for detecting changes in spectral qualities of dyes used is a multi-well microplate reader. Suitable devices are commercially available, for example, from Molecular Devices (SPECTRAMAX M2 fluorescence plate reader, $^{FLEXstationTM}$ microplate reader and fluid transfer system or $^{FLIPRTM}$ system), from HAMAMATSU (FDSS 6000), and PERKINELMER Life and Analytical Sciences (CellLuxTM).

Kit

Described herein is a kit for screening for an antibiotic. Such a kit can be used, for example, to screen a small molecule library for inhibitors of the $\sigma^E$ bacterial stress response. A typical kit for screening a library for an inhibitor of the $\sigma^E$ bacterial stress response (e.g., an antibiotic) includes a reporter strain as described herein, a substrate for containing the reporter strain, at least one control (e.g., negative control, positive control), and instructions for use.

In one embodiment, the kit for screening for an antibiotic includes at least one candidate antibiotic; a first bacterial strain including a nucleotide sequence. The nucleotide sequence contains a first nucleic acid encoding $\sigma^E$ and a second nucleic acid encoding RybB. The second nucleic acid is operably linked to the first nucleic acid and also contains at least one transcriptional terminator sequence disposed between the first and second nucleic acids. In addition, the nucleotide sequence contains a nucleotide sequence comprising a third nucleic acid encoding a reporter protein. The third nucleic acid is operably linked to a porin regulatory sequence. The first bacterial strain also encodes at least one mutation that permits the growth of the bacterial strain in the absence of $\sigma^E$ activity.

The kit also contains a second bacterial strain that includes a nucleotide sequence containing the third nucleic acid that encodes a reporter protein and at least one mutation that allows the growth of the bacterial strain in the absence of $\sigma^E$ activity. The third nucleic acid is operably linked to the porin regulatory sequence.

Also included in the kit is a solid substrate for containing the bacterial strains and instructions for use.

In one embodiment, a kit for identifying $\sigma^E$ pathway inhibitors includes a reporter strain, a control strain (e.g., a strain without rpoE and rybB so the reporter is always expressed), and reagents (e.g., chemicals) to turn on the system so the method can be performed. Such reagents can include IPTG (isopropyl-beta-D-thiogalactopyranoside) to induce expression of rpoE, and AHT (anhydrotetracycline) to induce expression of the reporter gene.

The kit can also include the secondary screening strains described herein to categorize inhibitors. Compounds that are small molecule inhibitors can also be included as positive controls.

Other embodiments of kits include a screen for inhibitors of other transcription factors and sRNAs. For such kits, changes to the existing plasmids described herein can be made as needed to facilitate cloning, for example. Such a modified kit can include the following: a plasmid encoding rpoE functionally linked to rybB could be included. A transcription factor of interest can be cloned in place of rpoE and/or an sRNA of interest can replace RybB sRNA. Also, a plasmid encoding yfp reporter can be included. The regulatory sequence targeted by their chosen sRNA upstream of yfp could be cloned. A control plasmid that does not include a transcription factor and sRNA to be used for unregulated expression of the reporter can be included. Also, an E. coli strain could be included for performing the method in; a user of the kit can transform the plasmids described above into this strain.

Optionally, kits can also contain one or more of the following: containers that include positive controls, containers that include negative controls, photographs or images of representative examples of positive results and photographs or images of representative examples of negative results.

Additional Uses for the Inhibitors Described Herein

Compounds can be used as anti-bacterial microbiocides for applications other than as pharmaceuticals. Contemplated applications include incorporation in or surface coating of materials for medical use such as stents or artificial valves or in non-medical devices, inclusion in other formulations to provide microbiocidal activity such as additives for cleaning solutions, and water treatment. For example, a composition including an inhibitor of a bacterial stress response identified by the methods described herein can be used to inhibit bacterial growth on a solid surface. A solid surface (e.g., at least one surface of a medical device) can be coated with a composition including an inhibitor of a bacterial stress response in an amount effective for inhibiting bacterial growth on the solid surface.

Data and Analysis

Use of the composition, method and kit described herein can employ conventional biology methods, software and systems. Useful computer software products typically include computer readable medium having computer-executable instructions for performing logic steps of a method. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2nd ed., 2001). See also U.S. Pat. No. 6,420,108.

The composition, method and kit described herein can also make use of various computer program products and software for a variety of purposes, such as reagent design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Additionally, the embodiments described herein include methods for providing data (e.g., experimental results, analyses) and other types of information over networks such as the Internet.

EXAMPLES

The present invention is further illustrated by the following examples. The examples are provided for illustration only and should not be construed as limiting the scope of the invention in any way.

Example 1

Developing Novel Broad-Spectrum Antibiotics

Testing optimized cyclic peptides and inhibitors for antibacterial activity against various pathogens: Inhibitors obtained using this method are added exogenously to bacterial species of interest to determine the minimal inhibitory activity (MIC) and minimum bactericidal concentration (MBC) for those inhibitors with bacteriostatic or bactericidal activity. Inhibitors are also added exogenously to bacterial species of interest to evaluate the compounds' abilities to inhibit $\sigma^E$ activity and sRNA-Hfq targeted degradation of target mRNAs.

Acquisition of resistance to antibiotic cyclic peptides and inhibitors: The rate at which bacteria can acquire resistance to an antibiotic also contributes to long-term drug efficacy. For this purpose bactericidal and bacteriostatic inhibitors are monitored for resistance acquisition. Bacteria are plated on media with and without the inhibitors to determine the frequency of resistance mutations. Resistance rates on the order of 1 in $10^{-6}$ or lower are considered to be effective. Higher rates indicate that resistant subpopulations are present in the starting culture, suggestive of a less effective drug candidate. Acquisition of resistance to inhibitors of $\sigma^E$ activity and sRNA-Hfq targeted degradation of target mRNAs that are not non-bacteriostatic or bactericidal are performed using the yfp fluorescence reporter method described herein. One bacterial culture is grown continuously in the presence of the inhibitor and one is propagated without the inhibitor. The percentage of cells in each culture whose $\sigma^E$ pathway is susceptible to the inhibitors (indicated by high fluorescence) is determined. If the cells grown in the presence of the inhibitor have a lower percentage with high fluorescence, the resistant strains were selected. Those inhibitors that exhibit a high rate of resistance acquisition are likely to be less effective drug candidates.

Example 2

Method for HTS to Identify Small Molecule Inhibitors of Two Key Steps in the $\sigma^E$ Pathway Described herein is the development of a method for HTS to identify small molecule inhibitors of two key steps in the $\sigma^E$ pathway: $\sigma^E$-dependent transcription, and regulation of porin mRNA levels by the protein Hfq in conjunction with $\sigma^E$-dependent sRNAs. Studies of genetic mutations in components of this pathway have led to a basic understanding of how the pathway functions. However, this approach is limited because it is difficult to distinguish direct functions of the pathway from the pleiotropic effects caused by the mutations. Small molecule inhibitors will enable experiments to test the function and molecular mechanism of this important pathway in greater detail.

Guided by the strong data described herein, the objective is attained by pursuing two specific aims: 1) optimize an method for high-throughput screening to identify molecules that specifically inhibit two key components of the $\sigma^E$ pathway; and 2) adapt and develop methods for secondary screening. A primary method that has been developed and tested in a pilot screen is optimized for use in a high-throughput format. Existing methods are adapted for use in secondary screens to eliminate false positive hits and to identify the molecules targeted by each inhibitor. The methods are submitted to Molecular Libraries Production Centers Network (MLPCN) for implementation. This approach is innovative in part due to its simultaneously targeting of a transcription factor, $\sigma^E$, and sRNA regulators that are required for a concerted physiological response to environmental challenges. All components of this pathway are highly conserved, so inhibitors identified here can be used to study the role of this pathway in growth and virulence of many pathogens. These inhibitors also provide lead compounds for antibiotic development.

The $\sigma^E$ system is a critical regulatory pathway that mediates the response to stress in the cell envelope of Gram-negative bacteria by altering the expression of porin genes and the maturation of porin proteins. In *E. coli*, $\sigma^E$ transcribes at least two sRNAs that influence porin expression, rybB and micA (17, 18, 30). RybB targets the ompC and ompW porin mRNAs for degradation, while MicA promotes degradation of the ompA mRNA and to a lesser extent the ompX mRNA (17, 18, 30). The sRNAs work in conjunction with the RNA chaperone protein Hfq. The protein Hfq binds the sRNAs to protect them from degradation, and facilitates interaction of the sRNAs with their target mRNAs (3). Hfq also binds to RNase E, ultimately leading to degradation of the mRNA by RNase E (3).

In addition to regulating the production of porins via RybB and MicA, $\sigma^E$ transcribes chaperones required for porin biogenesis (2). Therefore, changes in the activity of the $\sigma^E$ system are manifested in the levels of OmpC, OmpW and OmpA porins. Because porin levels are difficult to monitor in a HTS-compatible method, the present method was developed in which the gene encoding the fluorescent protein YFP was fused to the regulatory sequences of ompC (ompC'-yfp) (FIG. 1).

When $\sigma^E$ is active, it transcribes RybB. RybB, bound to Hfq, targets the ompC'-yfp mRNA for degradation, resulting in cells with little fluorescence. Alternatively, when $\sigma^E$ or RybB-Hfq is inhibited, ompC'-yfp mRNA is stable and YFP is produced, resulting in highly fluorescent cells. This scheme is particularly powerful because the method relies on a positive read-out, gain of fluorescence, rather than loss of signal. Therefore, false positive hits due to molecules that interfere with production of the reporter or growth of the method strain are not recovered.

Results

Figure 2:
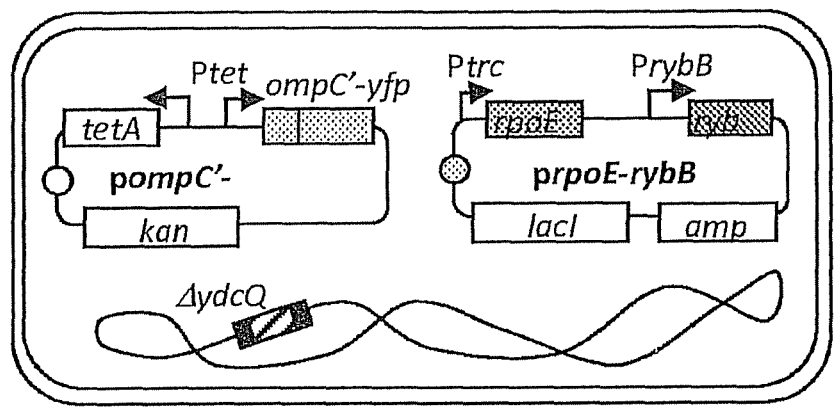
FIG. 2 is a schematic of a screening strain as described herein. The strain contains 2 plasmids prpoE-rybB encoding $\sigma^E$ and RybB with two strong transcription terminators between the genes. ompC'-yfp encodes the reporter gene. The chromosomal ΔydcQ mutation allows growth in the absence of $\sigma^E$ activity.

Construction of the bacterial strain: The screen is performed in strain SEA63810, a derivative of the *E. coli* K12 laboratory strain, MG1655. This strain is non-pathogenic and easy to grow, making it ideal for HTS. Because $\sigma^E$ activity is essential in MG1655, SEA63810 contains a known suppressor, ΔydcQ, to allow cells to live without $\sigma^E$ activity (4). Two plasmids carry the genes required for the reporter system, and inducible promoters allow titration of key factors to optimize readout. One plasmid carries the ompC'-yfp gene, under control of the tightly regulated Ptet promoter (FIG. 2). Expression of ompC'-yfp is induced by addition of anhydro-tetracycline (AHT). The other plasmid carries rpoE, the gene encoding $\sigma^E$, under control of the IPTG-inducible Ptrc promoter, and rybB under the control of its native $\sigma^E$-dependent promoter (FIG. 2). Addition of IPTG induces expression of $\sigma^E$, which then transcribes rybB. To determine the maximum fluorescence that can be produced from the reporter under screening conditions, an isogenic control strain was constructed that contains the ompC'-yfp reporter plasmid and an empty vector lacking rpoE and rybB. In the control strain, ompC'-yfp mRNA is not targeted for degradation and YFP expression is maximal.

The method is facile to use. One of skill simply mixes, measures and adds IPTG and AHT. By altering the concentration of IPTG and AHT that is added, the sensitivity of the method can be optimized for HTS.

Preliminary Method Validation. The maximum signal intensity for the method is determined by the amount of YFP produced when the $\sigma^E$ system is fully inhibited. Full inhibition is mimicked for method development purposes by the control strain described above. The background signal for the screen is defined by the YFP fluorescence in the screening strain in the absence of inhibitors (this signal comes from ompC'-yfp mRNA that is translated and escapes targeting for degradation by RybB-Hfq). Key parameters, including growth conditions, growth media, concentration and timing of addition of IPTG and AHT, have been adjusted to increase the maximum signal intensity while minimizing the background signal.

Figure 3:
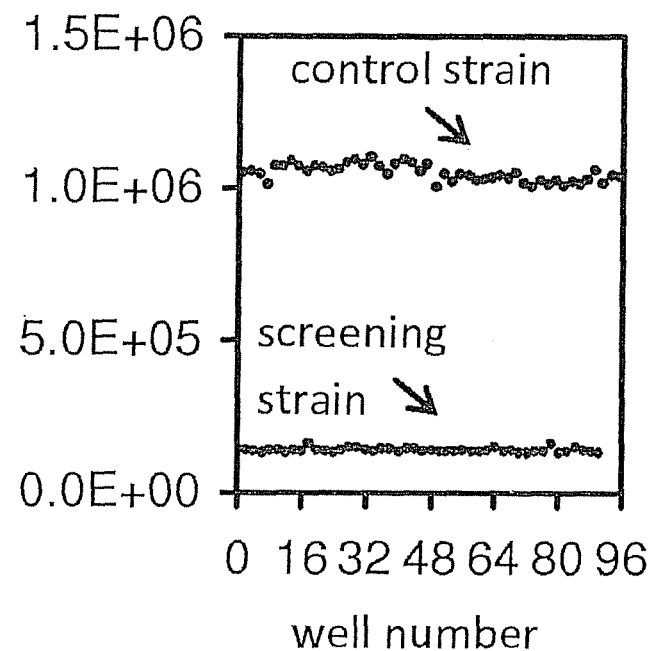
FIG. 3 is a plot of fluorescence intensity signals per well. The screening strain and control strain were arrayed in a 96 well microtiter plate. Fluorescence intensity signals from individual wells are shown.

To test the method, cultures of the screening strain and the control strain were grown at 30° C. to early exponential phase, and IPTG was added to a final concentration of 1 mM. About 45 min after IPTG addition, AHT was added to a final concentration of 100 ng/ml. When aliquoted into a microliter plate, YFP fluorescence was readily detected within 2.5 hours using a Spectramax M2 fluorescence plate reader (ex 500 nm, em 540, em cutoff 530 nm) (FIG. 3). Measurements of sensitivity, well-to-well variation, and day-to-day variation in a 96-well format produced parameters within the recommended ranges for HTS methods.

Studies performed on 3 different days in 96-well plates showed a signal-to-background ratio=6 (fluorescence of the control strain divided by that of the screening strain). The coefficients of variation (CV) for the signal intensities of the control and screening strains (standard deviation/mean) were both in the range of 2-5%. The Z' values for the method were reproducibly 0.9 ($Z'=1-(3\sigma_{c+}3\sigma_{c-})/|(\mu_{c+}-\mu_{c-})|$, where c+ is the control strain and c− is the screening strain). Similar results were recently obtained with 20 µl method volume in 384-well plates. These results provide high confidence that the method s successful under HTS-compatible conditions.

Pilot Screen: To ensure that inhibitors of the $\sigma^E$ system can be obtained with the method, the screening strain was used to identify inhibitor's from a library of cyclic peptides. Cyclic peptides can be produced in bacterial cells using SICLOPPS, an intein-based technology, and SICLOPPS has been used to generate libraries of cyclic peptides for screening (1).

A SICLOPPS library encoding ~$10^6$ different cyclic peptides was introduced into the screening strain, and cells with increased YFP fluorescence were isolated using fluorescence activated cell sorting (FACS). Eight isolates gave robust and reproducible inhibition. The sequences of the 8 cyclic peptides were determined, and intriguingly one of the peptides shares some sequence identity with the β subunit of RNA polymerase, suggesting that it could competitively inhibit association of $\sigma^E$ with RNA polymerase. These results indicate that the screening strain will identify inhibitors of the $\sigma^E$ system, and provide tools to evaluate the HTS method.

Two of the cyclic peptides were chemically synthesized and are being used to evaluate the dose-dependence of the method as described below. Epifluorescence microscopy and direct fluorescence measurements indicate that incubation of the screening strain with 100 µM concentration of either of the cyclic peptides increases YFP fluorescence to levels comparable to that of the control strain. The peptides increase YFP fluorescence to a lesser extent at 10 µM, and have little effect on fluorescence at 1 µM, suggesting that there is dose-dependent inhibition.

Tolerance to DMSO: To assess the sensitivity of the method to DMSO, the screening strain and control strain were grown in the presence of 1% DMSO. YFP fluorescence of the DMSO-treated cells was unchanged compared to that of untreated cells, demonstrating that DMSO does not interfere with the method. In addition, 1% DMSO does not alter the growth of either *E. coli* strain.

Further optimization of the method and configuration for HTS. The method will be optimized for HTS in high density format (384-well or 1,536-well plates). The results described herein show that the signal is sufficiently strong for a 384-well format (see above), but aeration properties in small well plates are different and can affect growth and gene expression.

First, conditions optimized for 96-well plates are tested in 384-well and 1536-well plates to determine if the signal-to-background ratio, well-to-well and day-to-day variation, and Z' values are appropriate for HTS. If these parameters indicate that further optimization is required prior to HTS, the incubation times with IPTG and AHT, the concentration of AHT, and the growth temperature (30° C. vs 37° C.) is varied until appropriate parameters are achieved. Given the strong data already generated, the robustness of the screening strain, and the ease and rapidity with which conditions can be varied, this step is readily accomplished. Once the method has been successfully adapted and validated for use in HTS format, a small molecule screen is performed.

Dose-dependent response: The method is also evaluated to ensure it has the appropriate sensitivity and dynamic range to respond in a dose-dependent manner to inhibitors. The dose-dependence of the method is assessed using two methods: 1) addition of cyclic peptide inhibitors isolated in the studies described herein and small molecules isolated in the pilot screen to be performed in collaboration with the Broad Institute and 2) altering the activity of $\sigma^E$, and therefore the readout of the system, using well-characterized variants of $\sigma^E$.

The cyclic peptides isolated in the genetic approach described herein are the only known synthetic inhibitors of either $\sigma^E$ or RybB-Hfq. The 8 identified inhibitory cyclic peptides are chemically synthesized using established methods that are routine (15). Cyclic peptides are added at concentrations from 10 mg/ml to 5 µg/ml to the screening strain in microtiter plates and grown under the optimized method conditions determined above. The reproducibility of inhibition is determined by comparing YFP fluorescence of wells that receive the same concentration of peptide, and the dose-dependence is determined by comparing YFP fluorescence of wells that receive different concentrations of the peptides.

Two cyclic peptides have already been synthesized, and results generated thus far indicate that these peptides increase YFP fluorescence of the screening strain in a dose-dependent manner. A method for dose-dependence will be repeated using small molecule inhibitors identified in the pilot screen. Given the results described herein, it is expected that increasing amounts of cyclic peptides or small molecules will results in increasing amounts of YFP.

The dose-dependence of the method is also evaluated using rpoE variants with point mutations that lower $\sigma^E$ activity. The L10P, V170M, and S172A point mutations are introduced into the rpoE gene on the prpoE-rybB plasmid. It has been shown that these mutations reduce $\sigma^E$ activity, as measured from a $\sigma^E$-dependent lacZ reporter, by 8, 15, and 47-fold, respectively. prpoE-rybB plasmids containing these mutations are transformed with the pompC'-yfp reporter plasmid into SEA63810 to produce test strains. YFP fluorescence is measured in the test strains and used to calibrate the dynamic range of the method, relating YFP read-out of the screening and control strains to known alterations in the level of $\sigma^E$ activity. If the method does not have the dynamic range and sensitivity to respond in a dose-dependent manner to the cyclic peptides, small molecules, or $\sigma^E$ variants, the method is reoptimized using the alternative approaches described below.

Several properties of the reporter strain can be altered if necessary. Two major factors affect the signal intensity, signal-to-noise ratio, and reproducibility of the method: the amount of YFP signal and the amount of RybB sRNA produced to target the reporter mRNA for degradation. These factors can be adjusted in several ways. The promoter driving expression of ompC'-yfp can be replaced by a stronger promoter if the signal is too weak. Likewise, the promoter driving expression of $\sigma^E$ can be replaced by a stronger promoter, if the background is too high. If YFP fluorescence is unstable or too weak, the yfp gene can be replaced by the gene encoding firefly luciferase, and luminescence used as the read-out. Should these manipulations be necessary, they can be rapidly accomplished.

Initial hits from HTS, potentially numbering in the tens of thousands, include inhibitors that act anywhere along the pathway from $\sigma^E$-dependent transcription of rybB to RybB-Hfq-targeted degradation of ompC'-yfp as well as false positive hits. To rapidly eliminate false positives and downselect and prioritize hits, three secondary screens are developed, each of which can be performed in HTS format or in large batches in microtiter plates. The secondary screens are based on methods already available (22, 29).

Secondary screen 1 will eliminate false positive hits that increase fluorescence independently of the $\sigma^E$ system. Remaining initial hits will be tested in secondary screens 2 and 3 to identify high priority compounds with strong inhibitory activities. Secondary screen 2 will identify hits that inhibit $\sigma^E$-dependent transcription, and secondary screen 3 will identify hits that inhibit RybB-Hfq activity. The methods from screens 2 and 3 will be repeated on high priority hits to determine the dose response of the $\sigma^E$ and RybB-Hfq inhibitors. Inhibitors that have the highest activity and exhibit a sigmoidal and saturable dose-response curve will be analyzed to determine the molecular target and used as pharmacological tools.

Figure 4:
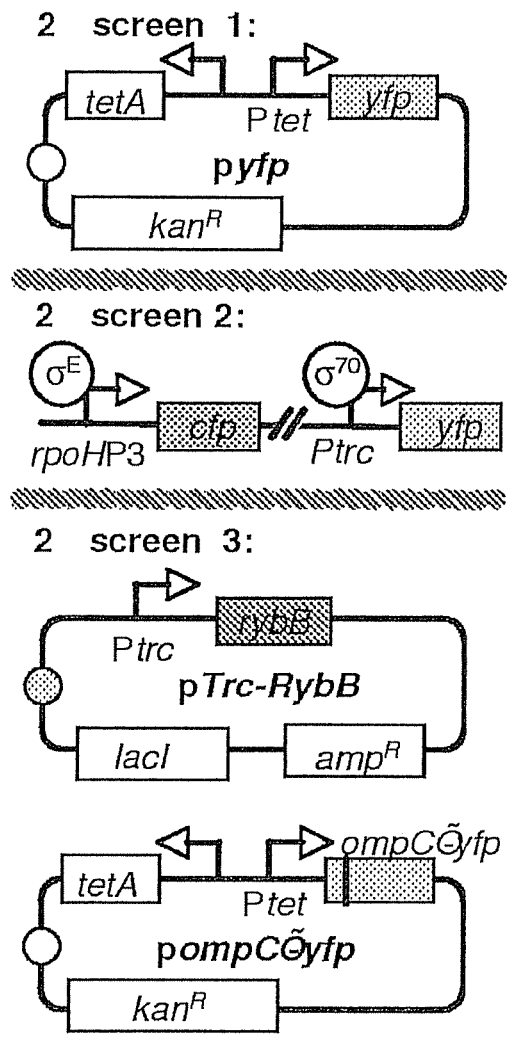
FIG. 4 is a schematic of secondary (2°) screens. Key components of each 2° screening strain are shown.

Secondary screen 1: Strain 2°-1 is used to eliminate false positive hits that increase YFP fluorescence independent of the $\sigma^E$ system. YFP is produced in this strain from the same plasmid and the same AHT-inducible promoter used in the primary screening strain. However, the ompC+ region has been removed so that YFP expression is no longer controlled by the $\sigma^E$ system (FIG. 4, top). The strain is incubated with initial hits from HTS, and YFP fluorescence is measured. This method is performed in HTS or large batch format. Molecules that do not alter YFP fluorescence are tested in secondary screens 2 and 3.

Secondary screen 2: Strain 2°-2 is used to identify hits that inhibit $\sigma^E$-dependent transcription. $\sigma^E$ activity is measured using a reporter fusion in which the cfp gene is transcribed from the $\sigma^E$-dependent rpoHP3 promoter (FIG. 4, middle). This promoter has been used extensively in lacZ fusion constructs to measure $\sigma^E$ activity. To control for effects on total transcription, transcription from the $\sigma^{70}$-dependent Ptrc promoter is measured using a yfp reporter in the same cells (FIG. 4, middle). Both reporters are integrated into the chromosome of the SEA63810 strain using standard molecular genetic techniques regularly employed (12).

If the intensity of CFP fluorescence in strain 2°-2 is too low to reliably measure inhibition, a deletion of rseA, encoding the inhibitor of $\sigma^E$, is engineered into the strain. Deletion of rseA hyperactivates $\sigma^E$, so the CFP signal is increased. To demonstrate that the secondary screen works, a potent inhibitor of $\sigma^E$ activity, RseA$_{cyto}$ (8), is expressed in the strain. CFP and YFP fluorescence are measured following overproduction of RseA$_{cyto}$ to verify that $\sigma^E$-dependent CFP and not $\sigma^{70}$-dependent YFP is reduced.

To identify inhibitors of $\sigma^E$-dependent transcription, strain 2°-2 are grown in the presence of the true positive hits verified in secondary screen 1. Hits that significantly reduce the CPF/YFP ratio, by lowering CFP, compared to the untreated strain are given top priority and evaluated in the dose response method described below. Hits that cause less than a 2-fold change are not pursued further. This method is simple mix and measure method and can be done in high-throughput format to screen thousands of compounds.

Secondary screen 3: Strain 2°-3 is used to identify hits that inhibit RybB-Hfq-dependent mRNA degradation. Strain 2°-3 uses the same ompC'-yfp reporter used in the primary method, however RybB is expressed from the $\sigma^{70}$-dependent Ptrc promoter on the pTrc99a plasmid, instead from its native $\sigma^E$-dependent promoter (FIG. 4, bottom).

To verify that strain 2°-3 can respond to inhibition of RybB activity, hfq is deleted. In the absence of Hfq, RybB is not active (30), so the reporter gene is expressed and YFP fluorescence is increased compared to cells with Hfq. This method is also a simple mix and measure method that can be performed in high-throughput format.

Strain 2°-3 is grown in the presence of the true positive hits verified in secondary screen 1, and IPTG and AHT added to induce expression of rybB and ompC'-yfp, respectively. Hits that cause <2-fold change are not pursued further. Hits that cause a >2-fold change in YFP fluorescence are prioritized based on the magnitude of the increase. Top priority hits, those with the highest increase in YFP, are evaluated in the dose response method described below. To further validate the secondary screens, they are used to evaluate cyclic peptide inhibitors and small molecules identified in the pilot screens.

Dose response methods. Dose response methods are used to ensure that inhibitors are well behaved and to prioritize compounds for downstream biochemical methods outlined below. The dose response methods are performed using strains 2°-2 and 2°-3 in high-throughput format or in large batches in microtiter plates. Top priority hits identified in secondary screens 2 and 3 are serially diluted, incubated with the appropriate secondary screening strain, and reporter fluorescence is measured.

Dose-response curves are generated for each compound. Compounds not exhibiting a sigmoidal and saturable dose-response curve will be discarded. In addition, hits with an $IC_{50}$>100 µg/ml are unlikely to be useful in biological methods and are of lower priority. Of the remaining compounds with sigmoidal and saturable dose-response curves, those with the lowest $IC_{50}$ and the largest percent inhibition are of high priority for further analysis.

Expected results. The work described here ensures that validated secondary methods are in place to eliminate false positive hits, classify the true positive hits as inhibitors of $\sigma^E$-dependent transcription or RybB-Hfq activity, and prioritize hits for use as pharmacological tools to explore cellular, physiological, and biochemical functions of the $\sigma^E$ system.

If the fluorescent reporters in the secondary screens are not of sufficient intensity for reproducible, accurate measurements, these promoters could be replaced with stronger ones. For example, the micA promoter can be used for $\sigma^E$-dependent constructs and the lacUV5 promoter for $\sigma^{70}$-dependent constructs.

The methods described above provide all the tools necessary for MLPCN screening to identify, classify, and prioritize inhibitors of the $\sigma^E$ system. In vitro methods are used to identify the molecular targets of the identified inhibitors. These methods are summarized here. The resulting group of small molecules with defined targets provide invaluable pharmacological tools to probe the basic biological and biochemical mechanisms of $\sigma^E$ and sRNA-Hfq activity. $\sigma^E$ inhibitors. Compounds that inhibit $\sigma^E$-dependent transcription could block transcription by $\sigma^E$ or reduce the cellular level of $\sigma^E$. Both sets of compounds are of interest because they probe different aspects of $\sigma^E$ function. Western blotting using existing polyclonal antibodies to $\sigma^E$ is used to determine the steady-state level of $\sigma^E$ in cells treated with the inhibitors. Standard multi-round in vitro transcription methods are used to identify compounds that reduce the production of $\sigma^E$-dependent transcripts (6, 25). To identify the strongest transcription inhibitors, $IC_{50}$'s are determined by adding increasing amounts of inhibitor to the transcription reactions. RybB-Hfq inhibitors. sRNA-Hfq targeting of mRNAs for degradation involves multiple steps, any of which can be targeted by the inhibitors. Having a set of inhibitors with defined targets is particularly useful to dissect the importance of each step for overall pathway function and cellular physiology. Inhibitors of the RybB-Hfq activity can affect binding of RybB to Hfq, formation of the trimeric complex between Hfq, RybB, and the target mRNA, or degradation of the targeted mRNA. Formation of RybB-Hfq and RybB-Hfq-mRNA complexes are monitored in gel shift methods using RNA components synthesized in vitro and purified Hfq (22, 29). Candidate inhibitors are added to the binding reactions to identify those that reduce complex formation. Degradation of mRNA by RNase E is performed in a RNA degradation method with purified RNase E (19). Candidate inhibitors are added to the degradation reactions to identify compounds that block RNase activity. For each set of methods, $IC_{50}$'s are determined to identify the strongest inhibitors. Hfq acts with many different sRNAs in the cell and inhibitors can be specific for its interactions with RybB or affect Hfq function with any sRNA. To test if a compound specifically inhibits RybB-Hfq activity, or affects other Hfq substrates, inhibition of MicA sRNA activity is tested. MicA targets ompA mRNA for degradation, whereas RybB targets ompC mRNA. Overexpression of RybB and MicA sRNAs reduces the steady state levels of their respective target mRNAs, which can be readily detected by Northern analysis (18). Inhibitors are added to cultures of strains overexpressing RybB or MicA. Inhibitors specific to RybB will stabilize ompC mRNA, whereas those that target Hfq acting with other sRNAs stabilize both ompC and ompA mRNAs. sRNA-Hfq mediated regulation of mRNA stability has important functions in bacteria in addition to the $\sigma^E$ pathway. Therefore, inhibitors that affect Hfq function with any sRNA provide novel reagents to address many questions about the biological mechanism of this pathway and provide lead compounds for antibiotics After HTS, hits are confirmed and the molecular targets are identified using the methods described above. Reagents obtained in this work provide invaluable tools to understand the molecular mechanisms by which the $\sigma^E$ system controls outer membrane porin composition and the role of the $\sigma^E$ system in bacterial physiology and pathogenesis. With these inhibitors it is possible to shut off different components of the $\sigma^E$ system in wild-type cells at different stages of growth, stress and pathogenesis, instead of using genetic mutations with pleiotropic effects. The inhibitors are also used to dissect the specific contribution of $\sigma^E$-dependent sRNAs to the $\sigma^E$ response. In addition, the antibiotic activity of $\sigma^E$ inhibitors is tested against bacteria in which $\sigma^E$ is essential for viability and the ability of both sets of inhibitors to reduce virulence of bacterial pathogens.

Example 3

Validation of an Method for HTS to Identify Small Molecule Inhibitors of Two Key Steps in the $\sigma^E$ Pathway In a method for HTS to identify small molecule inhibitors of two key steps in the $\sigma^E$ pathway ($\sigma^E$-dependent transcription and regulation of porin mRNA levels by the protein Hfq in conjunction with $\sigma^E$-dependent sRNAs), $\sigma^E$ directs transcription of the rybB sRNA in the screening strain described herein. RybB, bound to the Hfq protein targets the ompC'yfp reporter mRNA for degradation. When $\sigma^E$ and RybB are active, the reporter mRNA is degraded resulting in cells with little fluorescence. Alternatively, when $\sigma^E$ or RybB-Hfq is inhibited, ompC'-yfp mRNA will be stable and YFP will be produced, resulting in fluorescent cells. Further experimentation in addition to those experiments described above in Example 2 relating to this successful preliminary method was performed. First, validation was performed in 384-well plates, 15 µl/well. Also, dose-dependent response of the method was determined for three cyclic peptide inhibitors from the screen described in Example 2, demonstrating sensitivity of the method. In addition, initial versions of secondary screens to identify targets of inhibitors were developed and tested with cyclic peptides from the pilot screen. These additional experiments are described below.

In the studies described in Example 2, method validation had been performed on 150 µl samples in 96-well plates.

Figure 5:
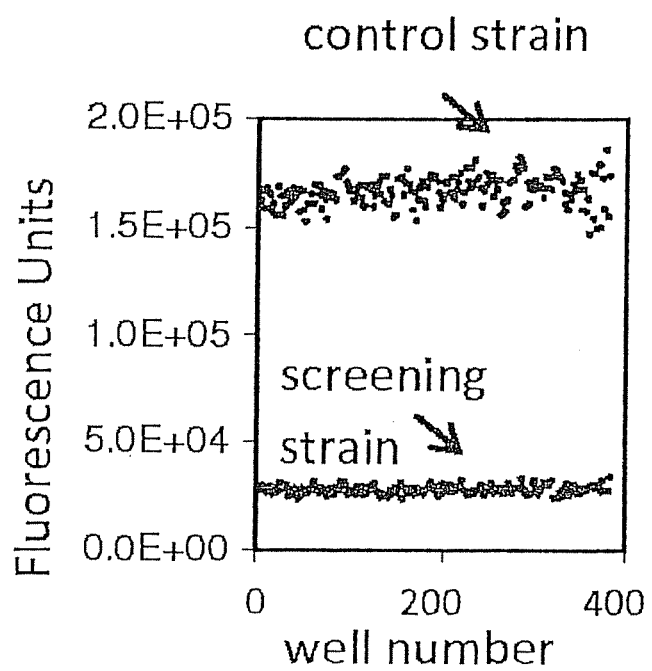
FIG. 5 is a plot of fluorescence intensity signals per well. The screening strain and control strain were arrayed in 384-well microtiter plates. Signals from individual wells are shown.

Subsequently, the method was tested using 1.5 μl samples in 384-well plates (FIG. 5). Cultures of the screening strain and the control strain were grown and fluorescence measured as described in the proposal. Studies performed on 3 different days showed a signal-to-background ratio=6.5±0.8 (fluorescence of the control strain divided by that of the screening strain). The coefficients of variation (CV) for the signal intensities of the control and screening strains were both within 4-8%. The Z' values for the method were 0.81±0.02. These results provide high confidence that the method will be successful under HTS-compatible conditions.

Three new cyclic peptides isolated in the pilot screen were synthesized and cyclized. Analyses of other cyclic peptide inhibitors from the screen described in Example 2 are ongoing.

Figure 6:
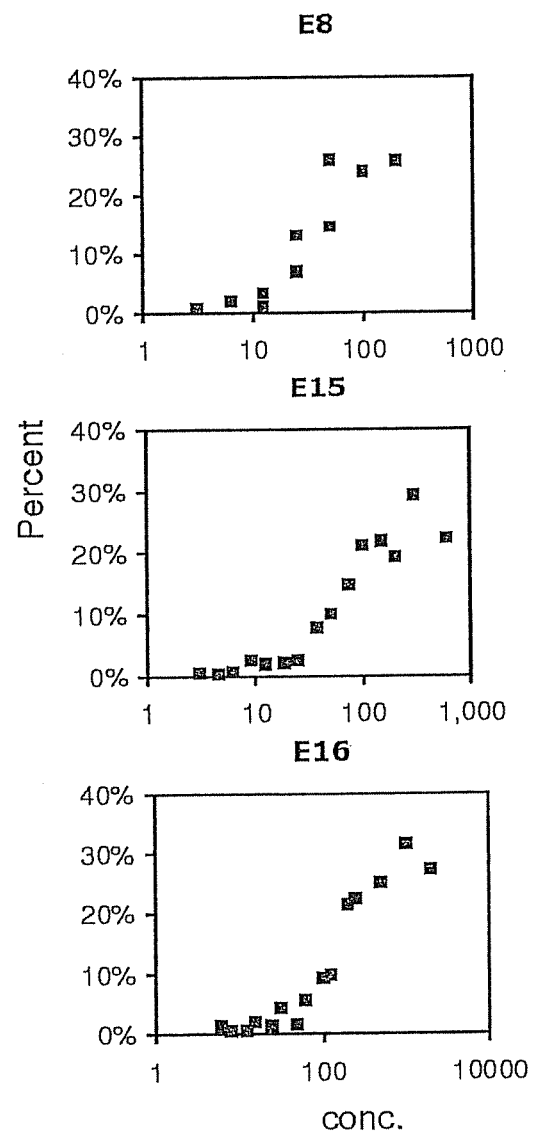
FIG. 6 is a series of graphs showing dose-dependence. Cyclic peptides were added to the screening strain at the indicated concentrations. Percent inhibition was determined relative to the control strain (100% inhibition-no degradation of ompC'yfp reporter mRNA). Data from two representative experiments are shown for each peptide.

The dose-dependence of the method was measured with each of the three newly made peptides (FIG. 6). These results demonstrate that the method has the sensitivity to detect different amounts of inhibition.

Figure 7:
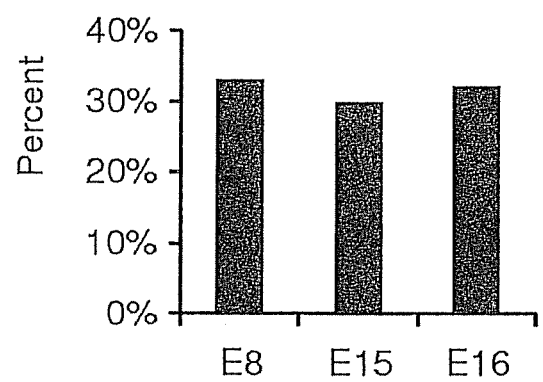
FIG. 7 is a graph showing inhibition of RybB-Hfq. Peptides were added to Strain 2°-3 at concentrations that gave near maximal inhibition with the screening strain (100 μM E8, 600 μM E15, 1 mM E16). Percent inhibition was determined relative to a control strain having the reporter but lacking RybB protein (100% inhibition-no degradation of ompC'yfp reporter mRNA).

As described in Example 2, secondary screens are used to identify the molecular targets of the inhibitors. Strains have been constructed to distinguish between inhibitors of $\sigma^E$-dependent transcription and inhibitors RybB-Hfq activity (analogous to Strain 2°-2 and Strain 2°-3 from Example 2 above). These strains were used to determine the targets of the cyclic peptides. The peptides were found to inhibit RybB-Hfq activity (FIG. 7). The percent inhibition measured in Strain 2°-3, which reports only on RybB-Hfq activity, is comparable to that seen in the primary screening strain, which reports on both $\sigma^E$-dependent transcription and RybB-Hfq activity.

Other Embodiments

Any improvement may be made in part or all of the composition, kit, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

References

1. Abel-Santos, E., C. P. Scott, and S. J. Benkovic. 2003. Use of inteins for the in vivo production of stable cyclic peptide libraries in *E. coli*. Methods Mol. Biol. 205:281-94.
2. Ades, S. E. 2008. Regulation by destruction: design of the sigmaE envelope stress response. Curr. Opin. Microbiol. 11:535-40.
3. Brennan, R. G., and T. M. Link. 2007. Hfq structure, function and ligand binding. Curr. Opin. Microbiol. 10:125-33.
4. Button, J. E., T. J. Silhavy, and N. Ruiz. 2007. A suppressor of cell death caused by the loss of sigmaE down-regulates extracytoplasmic stress responses and outer membrane vesicle production in *Escherichia coli*. J. Bacteriol. 189:1523-30.
5. Costanzo, A., and S. E. Ades. 2006. Growth phase-dependent regulation of the extracytoplasmic stress factor, sigmaE, by guanosine 3',5'-bispyrophosphate (ppGpp). J. Bacteriol. 188:4627-34.
6. Costanzo, A., H. Nicoloff, S. E. Barchinger, A. B. Banta, R. L. Gourse, and S. E. Ades. 2008. ppGpp and DksA likely regulate the activity of the extracytoplasmic stress factor sigmaE in *Escherichia coli* by both direct and indirect mechanisms. Mol. Microbiol. 67:619-32.
7. Davis, B. M., and M. K. Waldor. 2009. High-throughput sequencing reveals suppressors of *Vibrio cholerae* rpoE mutations: one fewer porin is enough. Nucleic Acids Res.
8. De Las Penas, A., L. Connolly, and C. A. Gross. 1997. The sigmaE-mediated response to extracytoplasmic stress in *Escherichia coli* is transduced by RseA and RseB, two negative regulators of sigmaE. Mol. Microbiol. 24:373-85.
9. Flannagan, R. S., and M. A. Valvano. 2008. *Burkholderia cenocepacia* requires RpoE for growth under stress conditions and delay of phagolysosomal fusion in macrophages. Microbiology 154:643-53.
10. Gruber, T. M., and C. A. Gross. 2003. Multiple sigma subunits and the partitioning of bacterial transcription space. Annu. Rev. Microbiol. 57:441-66.
11. Guillier, M., S. Gottesman, and G. Storz. 2006. Modulating the outer membrane with small RNAs. Genes Dev. 20:2338-48.
12. Haldimann, A., and B. L. Wanner. 2001. Conditional-replication, integration, excision, and retrieval plasmid-host systems for gene structure-function studies of bacteria. J. Bacteriol. 183:6384-93.
13. Hayden, J. D., and S. E. Ades. 2008. The extracytoplasmic stress factor, sigmaE, is required to maintain cell envelope integrity in *Escherichia coli*. PLoS ONE 3:e1573.
14. Heusipp, G., M. A. Schmidt, and V. L. Miller. 2003. Identification of rpoE and nadB as host responsive elements of *Yersinia enterocolitica*. FEMS Microbiol. Lett. 226:291-8.
15. Horswill, A. R., S, N. Savinov, and S. J. Benkovic. 2004. A systematic method for identifying small-molecule modulators of protein-protein interactions. Proc. Natl. Acad. Sci. USA 101:15591-6.
16. Humphreys, S., A. Stevenson, A. Bacon, A. B: Weinhardt, and M. Roberts. 1999. The alternative sigma factor, sigmaE, is critically important for the virulence of *Salmonella typhimurium*. Infect. Immun. 67:1560-8.
17. Johansen, J., M. Eriksen, B. Kallipolitis, and P. Valentin-Hansen. 2008. Down-regulation of outer membrane proteins by noncoding RNAs: unraveling the cAMP-CRP- and sigmaE-dependent CyaR-ompX regulatory case. J. Mol. Biol. 383:1-9.
18. Johansen, J., A. A. Rasmussen, M. Overgaard, and P. Valentin-Hansen. 2006. Conserved small non-coding RNAs that belong to the sigmaE regulon: role in down-regulation of outer membrane proteins. J. Mol. Biol. 364:1-8.
19. Mackie, G. A., a A. Coburn, X. Miao, D. J. Briant, A. Prud'homme-Genereux, L. M. Stickney, and J. S. Hankins. 2008. Preparation of the *Escherichia coli* RNase E protein and reconstitution of the RNA degradosome. Methods Enzymol. 447:199-213.
20. Mecsas, J., P. E. Rouviere, J. W. Erickson, T. J. Donohue, and C. A. Gross. 1993. The activity of sigma E, an *Escherichia coli* heat-inducible sigma-factor, is modulated by expression of outer membrane proteins. Genes Dev. 7:2618-28.
21. Mutalik, V. K, G. Nonaka, S. E. Ades, V. A. Rhodius, and C. A. Gross. 2009. Promoter strength properties of the complete sigma E regulon of *Escherichia coli* and *Salmonella enterica*. J. Bacteriol. 191:7279-87.
22. Papenfort, K., V. Pfeiffer, F. Mika, S. Lucchini, J. C. Hinton, and J. Vogel. 2006. SigmaE-dependent small RNAs of *Salmonella* respond to membrane stress by accelerating global omp mRNA decay. Mol. Microbiol. 62:1674-88.
23. Raivio, T. L. 2005. Envelope stress responses and Gram-negative bacterial pathogenesis. Mol. Microbiol. 56:1119-28.
24. Rhodius, V. A., W. C. Suh, G. Nonaka, J. West, and C. A. Gross. 2006. Conserved and variable functions of the sigmaE stress response in related genomes. PLoS Biol. 4:e2.
25. Ross, W., and R. L. Course. 2009. Analysis of RNA polymerase-promoter complex formation. Methods 47:13-24.
26. Rowley, G., M. Spector, J. Kormanec, and M. Roberts. 2006. Pushing the envelope: extracytoplasmic stress responses in bacterial pathogens. Nat. Rev. Microbiol. 4:383-94.
27. Ruiz, N., D. Kahne, and T. J. Silhavy. 2006. Advances in understanding bacterial outer-membrane biogenesis. Nat. Rev. Microbiol. 4:57-66.
28. Sauter, C., J. Basquin, and D. Suck. 2003. Sm-like proteins in Eubacteria: the crystal structure of the Hfq protein from *Escherichia coli*. Nucleic Acids Res. 31:4091-8.
29. Sharma, C. M., and J. Vogel. 2009. Experimental approaches for the discovery and characterization of regulatory small RNA. Curr. Opin. Microbiol. 12:536-46.
30. Thompson, K. M., V. A. Rhodius, and S. Gottesman. 2007. SigmaE regulates and is regulated by a small RNA in *Escherichia coli*. J. Bacteriol. 189:4243-56.
31. Valentin-Hansen, P., J. Johansen, and A. A. Rasmussen. 2007. Small RNAs controlling outer membrane porins. Curr. Opin. Microbiol. 10:152-5.

We claim:

1. A system for identifying inhibitors of a bacterial stress response comprising:
   A) at least one candidate inhibitor of a bacterial stress response;
   B) a first bacterial strain including:
      a) a nucleotide sequence comprising:
         i) a first nucleic acid encoding $\sigma^E$;
         ii) a second nucleic acid encoding RybB, wherein the second nucleic acid is operably linked to the first nucleic acid,
         iii) at least one transcriptional terminator sequence disposed between the first and second nucleic acids;
      b) a nucleotide sequence comprising a third nucleic acid encoding a reporter protein, wherein the third nucleic acid is operably linked to a porin regulatory sequence;
   C) a second bacterial strain of the same species as the first bacterial strain including a nucleotide sequence comprising the third nucleic acid encoding a reporter protein and at least one mutation that allows the growth of the bacterial strain in the absence of $\sigma^E$ activity, wherein the third nucleic acid is operably linked to the porin regulatory sequence;
   D) a culture medium that is used both for the first bacterial strain and the second bacterial strain; and
   E) a means for detecting, measuring, and comparing expression of the reporter protein wherein an mRNA encoding the reporter protein is degraded.

2. The system of claim 1 further comprising a means for isolating and identifying the inhibitors of the bacterial stress response.

3. The system of claim 1 wherein the reporter protein comprises a luminescent or fluorescent protein.

4. The system of claim 1 wherein the means for detecting and measuring expression of the reporter protein comprises a luminometer, a fluorometer or a fluorescence activated cell sorter.

5. The system of claim 1 wherein the at least one candidate inhibitor of a bacterial stress response comprises a small molecule.

6. The system of claim 1 wherein the at least one candidate inhibitor of a bacterial stress response comprises a cyclic peptide or a library of cyclic peptides.

7. The system of claim 1 wherein the first nucleic acid includes rpoE, the second nucleic acid includes rybB, and the porin regulator sequence comprises one or more ompC regulatory sequences.

8. A method of identifying inhibitors of a bacterial stress response comprising:
   A) providing one culture medium containing a first bacterial strain including:
      a) a nucleotide sequence comprising:
         i) a first nucleic acid encoding $\sigma^E$;
         ii) a second nucleic acid encoding RybB, wherein the second nucleic acid is operably linked to the first nucleic acid;
         iii) at least one transcriptional terminator sequence disposed between the first and second nucleic acids;
      b) a nucleotide sequence comprising a third nucleic acid encoding a reporter protein, wherein the third nucleic acid is operably linked to a porin regulatory sequence;
   B) providing a second bacterial strain in the one culture medium of the first bacterial strain, the second bacterial strain including a nucleotide sequence comprising the third nucleic acid encoding a reporter protein and at least one mutation that allows the growth of the second bacterial strain in the absence of $\sigma^E$ activity, wherein the third nucleic acid is operably linked to the porin regulatory sequence;
   C) inducing protein expression of the first and second bacterial strains for $\sigma^E$;
   D) providing at least one candidate inhibitor of a bacterial stress response to the first and second bacterial strains;
   E) measuring the baseline expression of the reporter protein in the first and second bacterial strains;
   F) inducing protein expression of the first and second bacterial strains for the reporter protein wherein an mRNA encoding the reporter protein is degraded;
   G) measuring the expression of the reporter protein in the first and second bacterial strains;
   H) comparing the expression of the reporter protein in the first and second bacterial strains; and
   I) isolating and identifying the at least one candidate inhibitor of a bacterial stress response that does not inhibit expression of the reporter protein.

9. The method of claim 8 further comprising at least one secondary screen.

10. The method of claim 9 wherein the at least one secondary screen comprises bacterial strains constructed to distinguish between inhibitors of $\sigma^E$-dependent transcription and inhibitors RybB-Hfq activity.

11. The method of claim 8 wherein at least one bacterial strain comprises a reporter fusion in which a cfp gene is transcribed from a $\sigma^E$-dependent rpoHP3 promoter.

12. The method of claim 8 wherein at least one bacterial strain comprises an ompC'-yfp reporter and an $\sigma^{70}$-dependent Ptrc promoter.

13. The method of claim 8 wherein the reporter protein is a fluorescent or luminescent protein.

14. The method of claim 8 wherein the reporter protein is YFP.

15. The method of claim 8 wherein the at least one candidate inhibitor of a bacterial stress response is a small molecule, a cyclic peptide or cyclic peptide library.

16. The method of claim 8 wherein the first nucleic acid comprises rpoE, the second nucleic acid comprises rybB, and the porin regulator sequence comprises ompC regulatory sequences.

* * * * *